United States Patent [19]

Conaway et al.

[11] Patent Number: 5,073,638

[45] Date of Patent: Dec. 17, 1991

[54] PROCESS FOR THE PRODUCTION OF 2-THIOCYANOMETHYLTHIOBENZO-THIAZOLE

[75] Inventors: Lawrence S. Conaway, Dundee, Miss.; Marc F. Nagel, Memphis; John D. Pera, Cordova, both of Tenn.

[73] Assignee: Buckman Laboratores International, Inc., Memphis, Tenn.

[21] Appl. No.: 587,655

[22] Filed: Sep. 26, 1990

Related U.S. Application Data

[63] Continuation of Ser. No. 268,476, Nov. 4, 1988, abandoned.

[51] Int. Cl.⁵ .................................. C07D 277/74
[52] U.S. Cl. .................................................. 548/169
[58] Field of Search ................................. 548/169

[56] References Cited

U.S. PATENT DOCUMENTS

| | | | |
|---|---|---|---|
| 3,463,785 | 8/1969 | Buckman | 548/169 |
| 3,520,976 | 7/1970 | Buckman | 548/169 |
| 3,669,981 | 6/1972 | Pera | 548/169 |
| 4,755,609 | 7/1988 | Schade | 548/169 |

FOREIGN PATENT DOCUMENTS

| | | |
|---|---|---|
| 3504966 | 8/1986 | Fed. Rep. of Germany . |
| 3702671 | 3/1988 | Fed. Rep. of Germany . |
| 60-132695 | 7/1985 | Japan . |
| 60-132971 | 7/1985 | Japan . |

*Primary Examiner*—Robert Gerstl
*Attorney, Agent, or Firm*—Finnegan, Henderson, Farabow, Garrett, Dunner

[57] ABSTRACT

A process for the manufacture of 2-thiocyanomethylthiobenzothiazole. 2-Chloromethylthiobenzothiazole is reacted, in the presence of at least one glycol ether as a solvent for the reaction, with either an alkali metal or an ammonium thiocyanate at a temperature and for a time sufficient to produce the 2-thiocyanomethylthiobenzothiazole.

14 Claims, No Drawings

PROCESS FOR THE PRODUCTION OF 2-THIOCYANOMETHYLTHIOBENZOTHIAZOLE

This application is a continuation of application Ser. No. 07/268,476, filed Nov. 4, 1988, now abandoned.

This invention relates to a process for the production of 2-thiocyanomethylthiobenzothiazole from 2-chloromethylthiobenzothiazole and an alkali metal thiocyanate or ammonium thiocyanate in the presence of a glycol ether solvent.

The compound 2-thiocyanomethylthiobenzothiazole (to be designated hereinafter as TCMTB) is a fully approved, registered, commercially available fungicide which is used as a preservative for tanned leather, for the prevention of mold growth on lumber and other surfaces, and as a microbicide in the pulp and paper and water treatment industries.

The first described synthesis of TCMTB was in U.S. Pat. Nos. 3,463,785 and 3,520,976, which patents also describe the composition and uses of the fungicide. In these patents, a method of preparation involved the reaction of chloromethylthiocyanate and sodium 2-mercaptobenzothiazole. U.S. Pat. No. 3,520,976 also disclosed the preparation of a 2-chloromethylthiobenzothiazole mixture from a metal salt of 2-mercaptobenzothiazole and a large excess of bromochloromethane in the presence of acetone as solvent. The 2-chloromethylthiobenzothiazole was then reacted with ammonium thiocyanate using acetone as a solvent to produce a product containing 81.5% of TCMTB.

Japanese Patent Application No. 60-132971 describes the production of TCMTB by the reaction of a water-soluble salt of 2-mercaptobenzothiazole with chloromethylthiocyanate in the presence of water and a phase transfer catalyst. One disadvantage of any process which uses chloromethylthiocyanate is that this intermediate is not commercially available. In addition, chloromethylthiocyanate is a powerful lachrymator and has a vile odor even at very low concentrations. Furthermore, it is a very toxic chemical with an acute oral LD50 of 14.7 milligrams per kilogram of body weight in male and female rats.

U.S. Pat. No. 3,669,981 describes the process for the production of 2-chloromethylthiobenzothiazole and contains a statement that this compound may be reacted with an alkali metal thiocyanate or ammonium thiocyanate in the presence of water and/or organic solvents to produce TCMTB.

U.S. Pat. No. 4,755,609 discloses a process wherein 2-chloromethylthiobenzothiazole was reacted with an alkali metal thiocyanate or ammonium thiocyanate in aqueous solution at elevated temperatures of 70° to 100° C. in the presence of a phase transfer catalyst. There are several disadvantages in this process. This reaction must be run at relatively high temperatures in order to obtain good yields, but the aqueous medium can require extended reaction times and under these conditions TCMTB tends to decompose in water.

When the reaction is cooled for further processing, the TCMTB can separate as an oily layer. This layer will be contaminated by the presence of some dissolved alkali metal chloride or ammonium chloride in water and also a portion of the phase transfer catalyst.

To obtain a pure product, it is necessary to dissolve the TCMTB layer in a water insoluble organic solvent and to then separate the organic layer from the aqueous contaminants. Alternatively, the TCMTB might be separated directly from the reaction mixture but, in this case, it will contain alkali metal chloride, water and phase transfer catalyst and some further processing will be required to purify the TCMTB.

If the technique of dissolving the TCMTB in a water insoluble organic solvent, such as methylene chloride, is used, the organic layer must be washed with water to remove the entrained alkali metal chloride, dried and distilled to remove the organic solvent.

If a low boiling organic solvent is used to facilitate distillation, problems of environmental pollution must be solved as the solvent is condensed and recycled. If a high boiling solvent is used, distillation will be more difficult and the TCMTB will be subject to temperatures that will cause decomposition.

Recently, German Patent Publication DE 3,702,671 reported a procedure whereby liquid halomethylthiobenzothiazole was reacted with an alkali metal thiocyanate or ammonium thiocyanate in the absence of a solvent and in the presence of a phase transfer catalyst, such as polyethylene glycol, polyethylene glycol monomethyl ether or polyethylene glycol dimethyl ether, at a temperature of 50° to 100° C. When the reaction has been completed, an aromatic solvent is added. Glycol ether may also be added as a co-solvent. The mixture is filtered to remove the by-product alkali metal chloride or ammonium chloride as well as excess and unreacted thiocyanate salt.

The major disadvantage of this solvent-free reaction is that a phase transfer catalyst is required. These catalysts increase the cost of the process. In addition, when the aromatic hydrocarbon solvent is added and the mixture filtered, some of the catalyst will appear in the filtrate which is the desired product of the process.

The patent uses a substantial quantity of catalyst, up to 20% of the 2-chloromethylthiobenzothiazole charge, and any carry-over into the product has the possibility of causing compatibility problems. Regulatory agencies will also require additional toxicology tests if the catalyst has any toxic effects. In contrast, the process of the present invention will produce a product with a minimum amount of additional impurities present.

When the reaction of 2-chloromethylthiobenzothiazole and inorganic thiocyanate is run in an organic solvent, the solvent usually chosen is either acetone, methyl alcohol or ethyl alcohol because these are the organic solvents mentioned in the chemical literature as satisfactory for the reaction of inorganic thiocyanates and organic halides for the production of organic thiocyanates.

These solvents all have low boiling points, and the by-product chloride salts are insoluble in the reaction mixture. These chloride salts can be removed by filtration and the TCMTB product will then be obtained as a solution in the low boiling point solvent.

The low boiling point solvents which can be used to conduct the reaction are flammable and in some cases very toxic. Since severe restrictions are placed on the shipment of commercial products containing flammable solvents, it is always a disadvantage to market such a product if alternative processes can be discovered.

It has also been known to sell formulations of TCMTB using glycol ethers as a sole or co-solvent. The formulation of TCMTB with glycol ether has, insofar as is known, always been subsequent to the manufacture of TCMTB.

It has been discovered that at least one glycol ether solvent can be used as a reaction solvent for the reaction of 2-chloromethylthiobenzothiazole with an alkali metal thiocyanate or ammonium thiocyanate to produce solutions of TCMTB that can be marketed without any elaborate purification procedures. We have found that glycol ethers are good solvents for the commonly used inorganic thiocyanates.

The reactions, moreover, can be run at moderate temperatures and high yields of the desired TCMTB can be obtained in a relatively short period of time.

The alkali metal chlorides and ammonium chloride produced as by-products are insoluble, depending on the temperature, in the reaction mixture and can be easily removed by filtration using commonly available commercial filters or by centrifugation using commercially available centrifuges. Furthermore, solutions of TCMTB that can be formed in the process of this invention contain a sufficient quantity of TCMTB so that it is not necessary to concentrate or purify these solutions to obtain a marketable product.

It is, therefore, a principal object of the present invention to obviate the disadvantages of the prior art processes and provide an improved process for the preparation of TCMTB wherein at least one glycol ether is utilized as a reaction solvent.

It is another object of the invention to provide a unique process for the preparation of a glycol ether solution of TCMTB suitable for sale as a commercial product.

These and other objects and advantages will become apparent as the description proceeds.

SUMMARY OF THE INVENTION

This invention is a process for preparing 2-thiocyanomethylthiobenzothiazole comprising the step of reacting 2-chloromethylthiobenzothiazole with either an alkali metal thiocyanate or ammonium thiocyanate in the presence of at least one glycol ether as a solvent for the reaction, at a temperature, preferably 50° to 100° C., and for a time sufficient to produce 2-thiocyanomethylthiobenzothiazole. When the reaction procedure is completed, the product TCMTB can be obtained as a concentrated solution in the glycol ether by separating the TCMTB solution from at least one insoluble by-product, such as an alkali metal chloride or ammonium chloride.

DETAILED DESCRIPTION OF THE PREFERRED EMBODIMENTS

The fungicide 2-thiocyanomethylthiobenzothiazole (TCMTB) is prepared in accordance with this invention by reacting 2-chloromethylthiobenzothiazole with an alkali metal thiocyanate or ammonium thiocyanate in the presence of at least one glycol ether as a solvent for the reaction.

The alkali metal is preferably sodium or potassium. Sodium, potassium, and ammonium salts of thiocyanic acid are all soluble in glycol ethers.

The intermediate 2-chloromethylthiobenzothiazole may be prepared from sodium 2-mercaptobenzothiazole and bromochloromethane as described in U.S. Pat. No. 3,669,981, the disclosure of which is specifically incorporated by reference herein.

The alkali metal thiocyanate and ammonium thiocyanate starting materials are commercially available or could be prepared by well-known methods by one of ordinary skill in the art.

Exemplary glycol ether solvents suitable in this invention include the monomethyl, monoethyl, monopropyl, monobutyl and monophenyl ethers of ethylene glycol and diethylene glycol; the monomethyl, monoethyl, monopropyl, monobutyl, and monophenyl ethers of propylene glycol, dipropylene glycol, and tripropylene glycol; and the dimethyl, diethyl, dipropyl and dibutyl ethers of ethylene glycol, diethylene glycol, propylene glycol, dipropylene glycol, and tripropylene glycol. These solvents are either commercially available or obtainable by one of ordinary skill in the art by well-known methods.

The process of this invention is preferably conducted at a temperature of from about 50° to 100° C. More preferably, the process is conducted at 60° to 80° C., and most preferably at 60° to 70° C.

The reactions are continued until the desired yield is obtained. A yield of more than 90% can generally be readily attained using reaction times of about 3 to 7 hours. The reaction time will vary with the temperature used but long reaction times in excess of twelve hours should be avoided to minimize decomposition.

When the reaction is complete, the temperature can be reduced to below 30° C at which temperature the by-product chloride salt will be present as a solid (insoluble) in the glycol ether - TCMTB. The solid salt can be removed by standard separation techniques, such as filtration or centrifugation. A filtrate or centrifugate may contain less than one percent of the chloride salt. The concentration of TCMTB contained in the final solution after separation will depend on the amount of solvent used.

The ratio of thiocyanate salt to 2-chloromethylthiobenzothiazole is preferably in the range of 0.8 to 1.2 moles of the thiocyanate salt per mole of 2-chloromethylthiobenzothiazole. Appreciable excess of thiocyanate salt will result in the salt being present as an impurity in the final product.

If desired, in one embodiment of the invention, the TCMTB produced by the process of the invention can be obtained as an essentially solvent-free product from the glycol ether reaction mixture by removing both the insoluble by-product, such as the chloride salt, and the glycol ether from the reaction mixture. The TCMTB will then be obtained as a viscous liquid ranging in purity from 80 to 90%.

However, the viscous liquid will crystallize under normal winter conditions in temperature climates. Since the product is normally shipped in 55 gallon drums or even larger containers it will then be necessary to warm the container to melt the contents if crystallization has occurred. This operation can lead to decomposition of the TCMTB if care is not used to control the warming operations.

For this reason, it is preferred to design the reaction procedure so that a concentrated solution of TCMTB is obtained in the glycol ether solvent. Concentrations in the range of 50 to 70% by weight are preferred. These glycol ether solutions are particularly desirable because the high concentrations of TCMTB are stable even in cold weather. The solutions can then be readily formulated with surfactants, stabilizers, dyes, and other solvents to make emulsifiable products, dilute solutions or microemulsions.

The shelf stability of TCMTB solutions in either diethylene glycol monomethyl ether or diethylene glycol monoethyl ether solvent has been found to be excellent. Samples of 60% TCMTB by weight in these glycol ethers were evaluated over ten weeks time under four thermal conditions: 50° C., 25° C., 4° C. and −15° C. No degradation was detected and only minor crystal growth was observed in the −15° C. samples a week after seeding with pure crystalline TCMTB.

The following examples illustrate the invention, but do not serve as limitations thereon.

EXAMPLE 1

A 500 mL, three-neck, round bottom flask equipped with a water-cooled condenser, mechanical stirrer, heating mantle and thermostatic control was charged with 172.4 g of technical grade 2-chloromethylthiobenzothiazole, 64.8 g of sodium thiocyanate and 48 g of diethylene glycol monomethyl ether. The mixture was agitated and heated to 70° C. and held at that temperature for one hour. A fifteen gram sample was removed at that time. A five gram aliquot was cooled to room temperature, filtered through a 0.45 micron nylon membrane and the filtrate was analyzed for TCMTB using an HPLC method. The amount of TCMTB in the diethylene glycol monomethyl ether solution represented a 78 percent yield.

The sampling procedure was repeated after three hours reaction and the TCMTB yield was found to be 94 percent. At the end of five hours the reaction was cooled and the sampling procedure was repeated a third time. The final yield of TCMTB was 98 percent.

EXAMPLE 2

The procedure described in Example 1 was repeated using seven other glycol ether solvents at a temperature of 70° C. The quantity of glycol ether solvent used amounted to 17% of the total reaction mass. The percent yield of TCMTB was determined after one, three, and five hours.

| Solvent | Yield of TCMTB (Percent) | | |
|---|---|---|---|
| | One Hour | Three Hours | Five Hours |
| Diethylene glycol monoethyl ether | 86 | 96 | 100 |
| Diethylene glycol monopropyl ether | 79 | 95 | 96 |
| Ethylene glycol monophenyl ether | 37 | 80 | 94 |
| Propylene glycol monomethyl ether | 84 | 100 | 100 |
| Dipropylene glycol monomethyl ether | 73 | 90 | 94 |
| Diethylene glycol dimethyl ether | 90 | 100 | 100 |
| Diethylene glycol diethyl ether | 70 | 100 | 100 |

EXAMPLE 3

A 2L, three-neck, round-bottom flask equipped with a water-cooled condenser, mechanical stirrer, heating mantle and thermostatic control was charged with 647 g of technical grade 2-chloromethylthiobenzothiazole, 244 g of sodium thiocyanate and 195 g of diethylene glycol monomethyl ether. The mixture was heated at 70° C. for five hours, cooled to 25° C. with a water bath and allowed to stand 30 minutes without agitation. The reaction mixture was transferred to a pressure filtration apparatus equipped with a 0.65 micron pore-size nylon membrane and filtered at 20 psig. The filtrate was weighed and analyzed and found to contain 76.3% of the TCMTB produced. The filter cake was then slurried with 195 g of diethylene glycol monomethyl ether at ambient temperature and passed through the filter again. This second filtrate was also weighed and analyzed and then combined with the original filtrate. The resulting solution contained 60% by weight of TCMTB and accounted for 92.1% of the TCMTB produced.

The original filter cake was again reslurried with 195 g of diethylene glycol monomethyl ether, filtered and analyzed. The filtrate contained 6.9% of the TCMTB produced.

Finally the filter cake was washed once more with methylene chloride to determine the residual TCMTB in the cake. Only 1.0% of the produced TCMTB was remaining in the cake.

What is claimed is:

1. A process for preparing 2-thiocyanomethylthiobenzothiazole consisting essentially of the steps of
   (a) reacting 2-chloromethylthiobenzothiazole with either alkali metal or ammonium thiocyanate in the presence of at least one glycol ether as a solvent for the thiocyanate, wherein the glycol ether is selected from the group consisting of the monomethyl, monoethyl, monopropyl, monobutyl and monophenyl ethers of ethylene glycol and diethylene glycol; the monomethyl, monoethyl, monopropyl, monobutyl, and monophenyl ethers of propylene glycol, dipropylene glycol, and tripropylene glycol; and the dimethyl, diethyl, dipropyl and dibutyl ethers of ethylene glycol, diethylene glycol, propylene glycol, dipropylene glycol, and tripropylene glycol, at a temperature and for a time sufficient to produce said 2-thiocyanomethylthiobenzothiazole in solution in the glycol ether and to produce at least one insoluble reaction by-product; and
   (b) separating said 2-thiocyanomethylthiobenzothiazole-glycol ether solution from said by-product to obtain a solution of 2-thiocyanomethylthiobenzothiazole in glycol ether.

2. A process as described in claim 1, wherein the solvent is selected from the group consisting of diethylene glycol monoethyl ether, diethylene glycol monopropyl ether, ethylene glycol monophenyl ether, propylene glycol monomethyl ether, dipropylene glycol monomethyl ether, diethylene glycol dimethyl ether and diethylene glycol diethyl ether.

3. A process as described in claim 1, wherein the solvent is diethylene glycol monomethyl ether.

4. A process as described in claim 1, wherein the solvent is diethylene glycol monoethyl ether.

5. A process as described in claim 1, wherein the solvent is propylene glycol monomethyl ether.

6. A process as described in claim 1, wherein the solvent is dipropylene glycol monomethyl ether.

7. A process as described in claim 1, wherein the solvent is diethylene glycol dimethyl ether.

8. A process as described in claim 1, wherein the solvent is diethylene glycol diethyl ether.

9. A process as described in claim 1, wherein the reaction temperature is maintained from 50° to 100° C.

10. A process as described in claim 9, wherein the reaction temperature is maintained from 60° to 70° C.

11. A process as described in claim 1, wherein said 2-thiocyanomethylthiobenzothiazole-glycol ether solution is separated from said by-product to obtain a solution of 2-thiocyanomethylthiobenzothiazole at concentration of 50 to 70 percent by weight in glycol ether.

12. A process as described in claim 1, wherein said process comprises the further steps of
   (c) washing said separated by-product with at least one glycol ether to obtain additional 2-thiocyanomethylthiobenzothiazole in glycol ether; and (d) combining said separated solution of 2-thiocyanomethylthiobenzothiazole in the glycol ether obtained in step (b) with said additional 2-thiocyanomethylthiobenzothiazole in glycol ether obtained by washing in step (c) to obtain a solution of 2-thiocyanomethylthiobenzothiazole at a concentration of from 40 to 65% by weight in glycol ether.

13. A process as described in claim 1, wherein the alkali metal thiocyanate is sodium thiocyanate.

14. A process as described in claim 1, wherein the alkali metal thiocyanate is potassium thiocyanate.

* * * * *